United States Patent [19]

Kikuchi et al.

[11] 4,075,021

[45] Feb. 21, 1978

[54] PHOTOSENSITIVE MATERIAL FOR COLOR PHOTOGRAPHY

[75] Inventors: Shoji Kikuchi; Takaya Endo; Teruo Kagami; Ryosuke Sato, all of Hino, Japan

[73] Assignee: Konishiroku Photo Industry Co., Ltd., Tokyo, Japan

[21] Appl. No.: 625,043

[22] Filed: Oct. 23, 1975

[30] Foreign Application Priority Data

Oct. 25, 1974 Japan ................................. 49-123105

[51] Int. Cl.$^2$ ......................... G03C 1/06; G03C 5/32; G03C 7/16

[52] U.S. Cl. ...................................... 96/95; 96/60 R; 96/22

[58] Field of Search ...................... 96/95, 22, 66.3, 60, 96/22, 3

[56] References Cited

U.S. PATENT DOCUMENTS

| | | | |
|---|---|---|---|
| 3,928,041 | 12/1975 | Fujiwhara et al. | 96/66.3 |
| 3,958,993 | 5/1970 | Fujiwhara et al. | 96/66.3 |
| 3,961,959 | 6/1976 | Fijiwhara et al. | 96/66.3 |

*Primary Examiner*—Mary F. Kelley
*Attorney, Agent, or Firm*—Bierman & Bierman

[57] ABSTRACT

The present invention discloses a multi-layer photosensitive material for color photography in which a compound capable of reacting with an oxidation product of a developing agent to release a substance promoting bleaching of developed silver at the bleaching or blixing step after the development treatment is incorporated into at least one layer constituting said photosensitive material.

17 Claims, No Drawings

PHOTOSENSITIVE MATERIAL FOR COLOR PHOTOGRAPHY

This invention relates to a photosensitive material for color photography in which a compound capable of reacting with an oxidation product of a developing agent to release a substance promoting bleaching of developed silver at the bleaching or bleach-fixing step after the development treatment is incorporated into at least one of layers constituting the photosensitive material.

Various promotors for promoting bleaching of developed silver have heretofore been proposed. For example, there can be mentioned those disclosed in British Pat. No. 926,569, British Pat. No. 1,170,973, British Pat. No. 1,192,481, British Pat. No. 1,201,571, West German Pat. No. 1,937,727, U.S. Pat. No. 3,241,966 and etc.

Most of these known promotors, however, are defective in that they are unstable in a bleaching bath or bleach-fixing bath and hence, maintenance of these bathes for always obtaining constant finishes is very difficult.

It is a primary object of the present invention to provide a novel bleach-promoting substance-releasing compound capable of reacting with an oxidation product of a developing agent to exhibit an activity of promoting bleaching of developed silver while not substantially inhibiting development and a multi-layer photosensitive material for color photography which comprises said bleaching-promoting substance-releasing compound, said multi-layer photosensitive material for color photography being characterized in that the time required for the bleaching treatment or bleach-fixing treatment can be shortened, the bleaching treatment or bleach-fixing treatment can be performed effectively even when the concentration of treating agents in the bleaching bath or bleach-fixing bath is low and hence, the efficiency of the bleaching treatment or bleaching fixation treatment can be highly enhanced.

As means for overcoming the above-mentioned defects involved in conventional bleaching promotors, there may be considered a method in which a bleaching promotor is maintained inactively in an emulsion in any way and it is activated when a photosensitive material is immersed in a treating bath.

Based on this technical concept, we have made research works and have now found that compounds represented by the following general formula

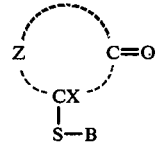

[I]

or $$R-CH-S-B \atop | \atop Y \qquad [II]$$

are compounds capable of releasing bleaching promotors at the development treatment step and effective for attaining the above object of the present invention.

In the above general formula [I], X is hydrogen or halogen and Z is a group of non-metallic atoms necessary for forming a 5-, 6- or 7-membered saturated or unsaturated carbon ring or nitrogen-, oxygen- or sulfur-containing heterocyclic ring. As specific examples of such non-metallic atom group, there can be mentioned rings of cyclopentanone, cyclohexanone, cyclohexenone, piperidones such as 2-piperidone, 3-piperidone and 4-piperidone, 4- to 7-membered lactones, lactams such pyrrolidone, and hydantoin. These carbon rings and heterocyclic rings are unsabstituted or substituted with at least one substituent selected from alkyl, aryl, alkoxy, aryloxy, acyl, halogen and the like. Further, these carbon rings and heterocyclic rings include those in which a fused ring is formed at an appropriate position, such as indanone, tetralone, benzocycloheptenone and oxyindole.

These carbon or heterocyclic rings can contain at least one —SB group (B is as defined below) on the carbon atom adjacent to the carbonyl group.

B is a group capable of forming, together with the sulfur atom, a heterocyclic mercapto compound which does not substantially inhibit development but has a bleaching promoting activity, when the thioether linkage is cleft at the development step. As typical instances of such heterocyclic mercapto compounds formed at the development step, there can be mentioned mercaptotetrazole compounds such as 1H-2-mercaptotetrazole, mercaptotriazole compounds such as 3-mercapto-1,2,4-triazole and 3-mercapto-4-phenyl-5-amino-1,2,4-triazole, mercapto-imidazoline compounds such as 2-mercaptoimidazoline, mercaptopyrimidine compounds such as 2-mercapto-4-aminopyrimidine, mercaptopurine compounds such as 2-amino-4-mercaptopurine, mercaptoquinolidine compounds such as 4-mercapto-4H-quinolidine and mercaptothiadiazole compounds such as 2-mercapto-5-amino-1,4,5-thiadiazole.

Typical instances of the compounds represented by the above general formula [I] are as follows:

I-1

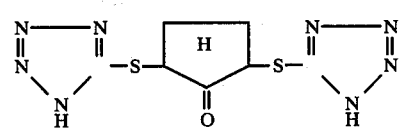

I-2

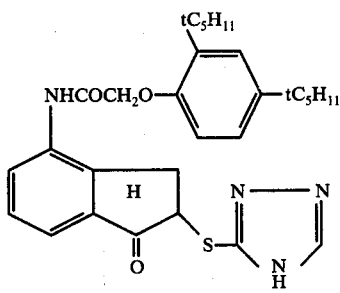

I-3

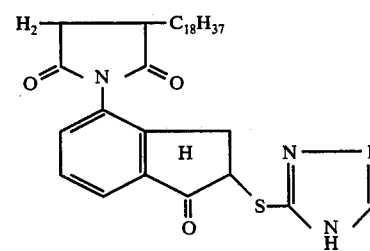

I-4

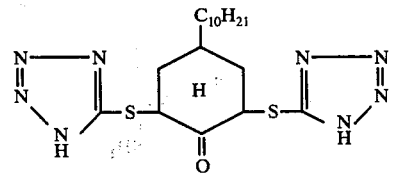

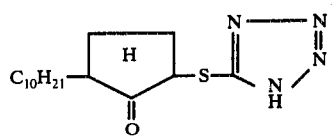
I-5

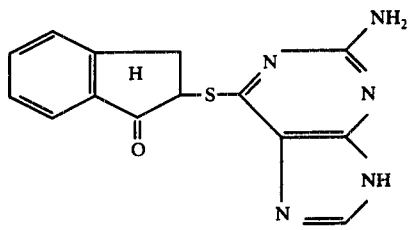
I-6

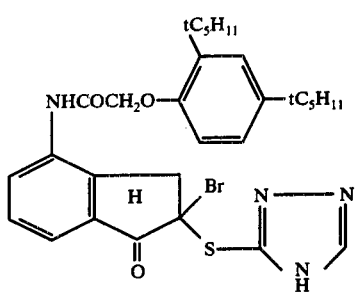
I-7

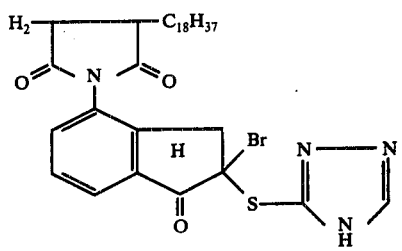
I-8

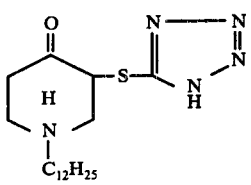
I-9

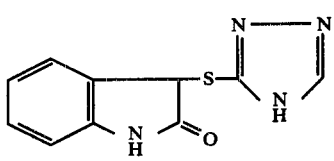
I-10

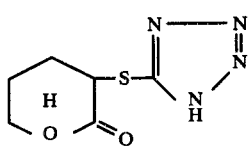
I-11

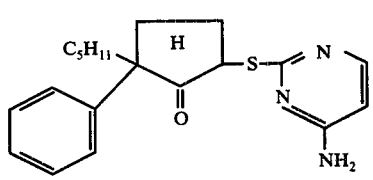
I-12

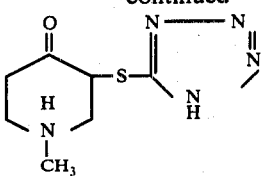
I-13

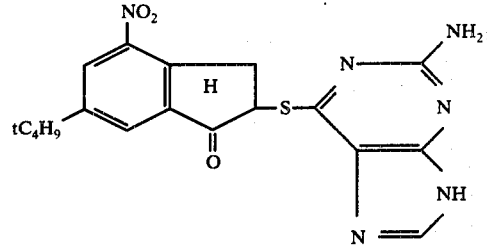
I-14

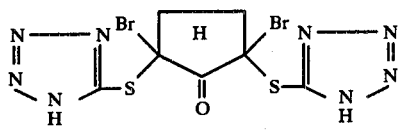
I-15

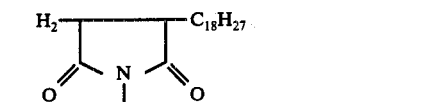
I-16

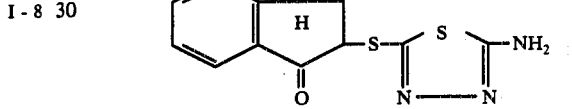
I-17

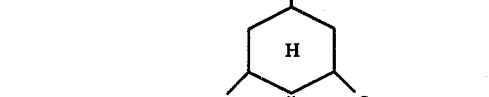
I-18

In the general formula [II], R is a member selected from

$R_3$ is alkyl, aryl or a heterocyclic residue, and in case R contains two of groups $R_3$, they may jointly constitute a group of atoms necessary for forming, together with the nitrogen atom, a nitrogen-containing heterocyclic ring nucleus. $R_4$ is alkyl.

Y is a group —O—$R_1$ or —COOR$_2$, in which $R_1$ is halogen, alkyl, aryl, acyl or a heterocyclic group and $R_2$ is alkyl. B is as sefined above in the general formula [I].

Specific examples of the compounds represented by the above general formula [II] are as follows:

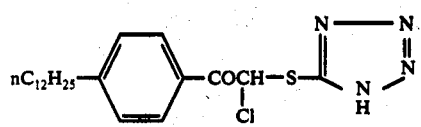 II-1

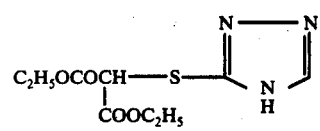 II-2

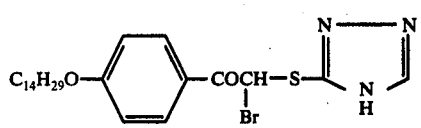 II-3

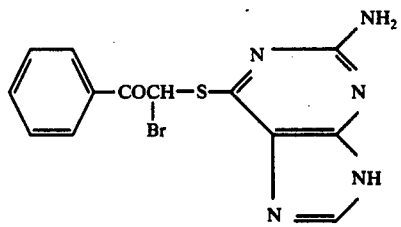 II-4

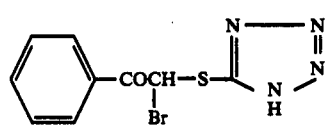 II-5

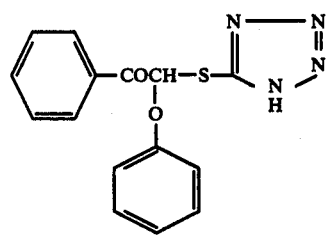 II-6

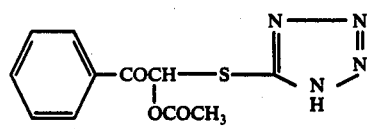 II-7

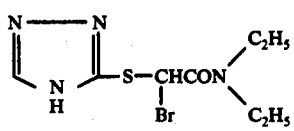 II-8

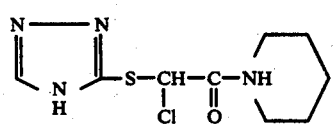 II-9

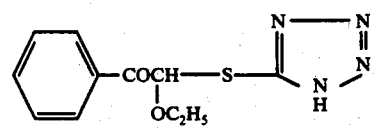 II-10

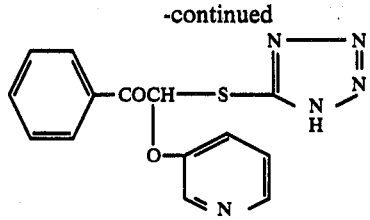 II-11

Compounds represented by the above general formulas [I] and [II] are compounds capable of reacting with an oxidation product of a color developing agent at the development step to release compounds having a bleaching-promoting activity. Even though these bleaching-promoting compounds are formed at the development step, they exhibit expected bleaching-promoting effect at the bleaching or bleach-fixing step. These compounds have a structure similar to the structure of so called development inhibitor-releasing compounds disclosed in, for example, Japanese Patent Applications Nos. 118892/72, 126217/72, 13811/73, 60411/74 and 77510/74, but they can be clearly distingushed over these known compounds in photographic properties, functions and hence object of use. More specifically, the bleaching-promoting substance-releasing compounds of the present invention are substantially free of the development inhibiting activity which is a characteristic property of the above-mentioned known development inhibitor-releasing compounds. In other words, the compounds of the present invention have none of the effects inherent of the development inhibitor-releasing compounds, namely the effects of improving the image granularlity and the sharpness, or they do not exhibit these effects to such an extent that these effects are actually observable.

Compounds formed by reaction of the bleaching-promoting substance-releasing compounds of the present invention with an oxidation product of a color developing agent are substantially colorless and therefore, incorporation of the compounds of the present invention into photosensitive materials for color photography causes no change of the color hue in dye images. Accordingly, the compounds of the present invention have an advantage that they can be incorporated into any of layers constituting a multi-layer photosensitive material for color photography.

Further, by the use of the compounds of the present invention, the time required for bleaching or bleach-fixing can be greatly shortened, or even if the treating agent concentration in a bleaching or bleach-fixing bath is low, the treatment can be accomplished effectively. Moreover, the compounds of the present invention brings about an advantage that they compensate an insufficient oxidative activity of oxidants of a relatively low oxidative activity such as an ethyenediamine tetraacetic-iron complex. Such oxidants are used with an aim of avoiding use of large amount of potassium ferricianate which causes environment pollution.

Typical examples of the process for synthesis of compounds represented by the general formulae [I] and [II] will now be illustrated.

SYNTHESIS EXAMPLE 1

Synthesis of Illustrative Compound 1-2:
A mixture of 46 g of 2-chloro-4-(2,4-di-t-amylphenoxyacetamido)-1-indanone and 13.5 g of a sodium salt of 3-mercapto-1,2,4-triazole was boiled under agitation for 6 hours in 700 ml of acetone. The solvent was removed by reduced pressure distillation and the residue was extracted with ethyl acetate. The ethyl acetate extract was dried with Glauber salt and the ethyl acetate was removed by reduced pressure distillation. The residue was separated and purified by column chromatography. Recrystallization from a mixed solvent of hexane and alcohol gave 10 g of the intended compound. Results of the elementary analysis of the product supported that the product was the intended compound.

SYNTHESIS EXAMPLE 2

Synthesis of Illustrative Compound I-7:

A solution formed by dissolving 26 g of 2-(1,3,4-triazolyl-2-thio)-4-(2,4-di-t-amylphenoxyacetamido)-1-indanone in 1 l of chloroform was agitated and 9 g of bromine was added dropwise to the solution at room temperature. The mixture was heated to 50° C. and agitated at this temperature for 1 hour. The solvent was removed by reduced pressure distillation, and the residue was recrystallized from alcohol to obtain the intended compound. Results of the elementary analysis of the product supported that the product was the intended compound.

SYNTHESIS EXAMPLE 3

Synthesis of Illustrative Compound II-5:

(a) Synthesis of α-(5-tetrazolylthio)-acetophenone:

In 500 ml of acetone was dissolved 40 g of α-bromoacetophenone, and 28 g of a sodium salt of 5-mercaptotetrazole was added to the solution. The mixture was boiled and agitated for 1 hour. The acetone was removed by reduced pressure distillation and the residue was extracted with ethyl acetate. The ethyl acetate was removed from the extract by distillation and the residue was recrystallized from alcohol to obtain the intended compound.

(b) Synthesis of α-bromo-α-(5-tetrazolylthio)-acetophenone:

In 1 l of acetic acid was dissolved 22 g of α-(5-tetrazolylthio)-acetophenone, and the temperature of the solution was elevated to 60° C. A solution of 16 g of bromine in 500 ml of acetic acid was added dropwise to the above solution under agitation from a dropping funnel. After completion of the dropwise addition, the mixture was agitated at the above elevated temperature of 60° C. for 3 hours. After completion of the reaction, the reaction mixture liquid was poured in ice water, and the precipitated crystal was recovered by filtration and washed with water sufficiently. The crystal was dried and recrystallized from alcohol to obtain the intended compound. Results of the elementary analysis of the product supported that the product was the intended compound.

SYNTHESIS EXAMPLE 4

Synthesis of Illustrative Compound II-6:

In 1 l of acetonitrile was dissolved 29.9 g of α-bromo-α-(5-tetrazolylthio)-acetophenone, and 13.2 g of a powder of a potassium salt of phenol was added to the solution. The mixture was boiled and agitated for 3 hours. After completion of the reaction, the reaction mixture liquid was subjected to reduced pressure distillation and the residue was extracted with ethyl acetate. The ethyl acetate was removed from the extract by reduced pressure distillation and the residue was recrystallized from methanol to obtain the intended compound. Results of the elementary analysis of the product supported that the product was the intended compound.

SYNTHESIS EXAMPLE 5

Synthesis of Illustrative Compound II-1:

In 1 l of chloroform was dissolved 38.8 g of α-(5-tetrazolylthio)-p-n-decylacetophenone, and 14.0 g of sulfuryl chloride was added to the solution and the mixture was boiled and agitated for 2 hours. After completion of the reaction, the chloroform was removed by distillation and the residue was recrystallized from alcohol and then from methanol to obtain the intended compound. Results of the elementary analysis of the product supported that the product was the intended compound.

Other illustrative compounds could be synthesized through the methods similar to the above-mentioned synthesis methods. Results of the elementary analysis made on the so synthesized illustrative compounds with respect to the sulfur atom are as shown in Table given below.

Table

| Illustrative Compound | Molecular Formula | Elementary Analysis Value for Sulfur Atom | |
|---|---|---|---|
| | | Calculated (%) | Found (%) |
| I - 1 | $C_7H_8N_8OS_2$ | 22.55 | 22.32 |
| I - 2 | $C_{29}H_{36}N_4O_3S$ | 6.16 | 6.50 |
| I - 3 | $C_{33}H_{48}N_4O_3S$ | 5.52 | 5.48 |
| I - 4 | $C_{18}H_{30}N_8OS_2$ | 14.62 | 14.78 |
| I - 5 | $C_{16}H_{28}N_4OS$ | 9.88 | 9.91 |
| I - 6 | $C_{14}H_{11}N_5OS$ | 10.78 | 10.82 |
| I - 7 | $C_{29}H_{35}BrN_4O_3S$ | 5.35 | 5.21 |
| I - 8 | $C_{33}H_{47}BrN_4O_3S$ | 4.86 | 4.99 |
| I - 9 | $C_{18}H_{33}N_5OS$ | 8.72 | 8.38 |
| I - 10 | $C_{10}H_8N_4OS$ | 13.81 | 13.72 |
| I - 11 | $C_6H_8N_4O_2S$ | 16.02 | 15.77 |
| I - 12 | $C_{20}H_{25}N_3OS$ | 9.02 | 9.27 |
| I - 13 | $C_7H_{11}N_5OS$ | 15.04 | 14.79 |
| I - 14 | $C_{18}H_{18}N_6O_3S$ | 8.05 | 8.10 |
| I - 15 | $C_7H_6Br_2N_8OS_2$ | 14.50 | 14.48 |
| I - 16 | $C_{18}H_{48}N_4O_3S_2$ | 14.82 | 14.76 |
| I - 17 | $C_{22}H_{30}N_4OS_2$ | 14.89 | 15.12 |
| I - 18 | $C_{17}H_{12}N_3F_{17}O_3S_3$ | 13.26 | 13.01 |
| II - 1 | $C_{21}H_{31}ClN_4OS$ | 7.58 | 7.32 |
| II - 2 | $C_5H_{13}N_3O_4S$ | 12.37 | 12.62 |
| II - 3 | $C_{24}H_{36}BrN_3O_2S$ | 6.28 | 6.50 |
| II - 4 | $C_{13}H_{10}BrN_5OS$ | 8.80 | 9.01 |
| II - 5 | $C_9H_7BrN_4OS$ | 10.72 | 10.69 |
| II - 6 | $C_{15}H_{12}N_4O_2S$ | 10.27 | 10.18 |
| II - 7 | $C_{11}H_{10}N_4O_3S$ | 11.52 | 11.56 |
| II - 8 | $C_8H_{13}BrN_4OS$ | 10.94 | 11.01 |
| II - 9 | $C_9H_{13}ClN_4OS$ | 12.30 | 12.51 |
| II - 10 | $C_{11}H_{12}N_4O_2S$ | 12.13 | 12.20 |
| II - 11 | $C_{14}H_{11}N_5O_2S$ | 10.23 | 10.35 |

The multi-layer photosensitive material for color photography according to the present invention include silver halide emulsion layers and especially, it has as structual layers at least one each of silver halide emulsion layers sensitized to red, green and blue spectral regions, respectively. Various known techniques adopted for incorporation of couplers can be utilized in the present invention for incorporation of the bleaching-promoting substance-releasing compound in the multi-layer photosensitive material for color photography.

For example, the bleaching-promoting substance-releasing may be dispersed in the form of fine particles in a layer by using it in the state dissolved in a high-boiling-point solvent. When this dispersion method is adopted, best results are obtained by using a low-boiling-point solvent in combination with the high-boiling-point solvent. It is possible to use the compound of the present invention represented by the formula [I] or [II] in the state mixed with a coupler or to disperse the compound of the present invention independently from a coupler. When a low-boiling-point solvent is employed, it can be removed from the resulting dispersion.

Solvents that can be used most preferably for the practice of the present invention will now be described.

As the high-boiling point solvent, there can be mentioned, for example, water-immiscible organic high-boiling-point solvents such as dibutyl phthalate, dioctyl phthalate, diisodecyl phthalate, triphenyl phosphate, tricresyl phosphate, diethyl laurylamide, dibutyl laurylamide, benzyl phthalate, monophenyl-p-t-butyl-phenyl phosphate, phenoxyethanol, diethylene glycol monophenyl ether, dimethoxyethyl phthalate and hexamethyl phosphoramide.

As the low-boiling-point solvent, there can be mentioned, for example, methylisobutyl ketone, $\beta$-ethoxyethyl acetate, methoxytriglycol acetate, acetone, methylacetone, methanol, ethanol, acetonitrile, dioxane, dimethylformamide, dimethylsulfoxide, ethyl acetate, butyl acetate, isopropyl acetate, butanol, chloroform, cyclohexane, cyclohexanol and fluorinated alcohols. These low-boiling-point solvents may be used instead of high-boiling-point solvents, or they may be used in combination with high-boiling-point solvents.

These solvents may be used singly or in the form of a mixture of two or more of these solvents.

When the compounds have a water solubility, it is possible to adopt a so-called Fisher method in which the compounds are used in the state dissolved in an alkali solution. When the compounds are incorporated in combination with a coupler, it is possible to incorporate in the same layer one of a coupler and the compound of the formula [I] or [II] by the dispersion method and the other by the Fisher method.

It is possible to incorporate the compound of the formula [I] or [II] not only in a silver halide emulsion layer but also in other layer such as an intermediate layer, a protective layer or the like. Most preferred results are obtained when the compound is incorporated in a silver halide emulsion layer.

In the multi-layer photosensitive material for color photography according to the present invention, the amount incorporated of the compound of the general formula [I] or [II] is changed depending on the kind of the photosensitive material used, the kind of the layer into which the compound is incorporated, the kind of the compound per se and other factors. For example, in case the compound is incorporated in a silver halide emulsion, it is generally preferred that the compound be incorporated in an amount of 0.3 to 20 g per Kg of the emulsion.

As the silver halide to be used for the multi-layer silver halide photosensitive material for color photography according to the present invention, there can optionally be employed any of silver halides customarily used in this field, for example, silver bromide, silver chlorobromide, silver iodobromide, silver chloroiodobromide and silver chloride. These silver halides may be of coarse particle size or fine particle size, and they may optionally be prepared according to any of conventional methods and further, a mixture of silver halides prepared according to different methods may be employed. It is preferred that soluble salts be removed from silver halide emulsions to be used in the present invention, but emulsions from which soluble salts are not removed can also be employed in the present invention.

As a hydrophilic colloid to be used effectively for formation of a photosensitive emulsion for the multi-layer silver halide photosensitive material for color photography according to the present invention, there can be mentioned, for example, gelatin, colloidal albumin, agar, gum arabic, alginic acid, hydrolyzed cellulose acetate acrylamide, imidated polyamides, polyvinyl alcohol, hydrolyzed polyvinyl acetate and gelatin derivatives (such as phenylcarbamyl gelatin, acylated gelatin, phthalated gelatin and gelatin grafted with an ethylene group-containing, polymerizable monomer such as acrylic acid, styrene, an acrylic acid ester, methacrylic acid or a methacrylic acid ester). These hydrophilic colloids can also be used effectively for formation of silver halide-free photographic structural layers such as filter layers, protective layers and intermediate layers.

The silver halide emulsion to be used for the multi-layer silver halide photosensitive material for color photography according to the present invention may be sensitized by various chemical sensitizing agents.

As such sensitizing agent, there can be employed, for example, activated gelatin, sulfur sensitizing agents (such as sodium thiosulfate, allylthiocarbamide, thiourea and allyl isocyanate), selenium sensitizing agents (such as N,N-dimethylselenourea and selenourea), reducing sensitizing agents (triethylene tetramine and stannic chloride) and noble metal sensitizing agents, for example, gold sensitizing agents (such as potassium chloroaurite, potassium aurothiocyanate, potassium chloroaurate and 2-aurosulfobenzothiazole methylchloride). In case a gold sensitizing agent is used, ammonium thiocyanate may be used as an auxiliary sensitizing agent. In addition, sensitizing agents of palladium, platinum or iridium salts (such as ammonium chloropalladate, potassium chloroplatinate and sodium chloropalladite) can be used singly or in combination with other sensitizing agents.

Blue-sensitive, green-sensitive and red-sensitive emulsions to be used for the multi-layer silver halide photosensitive material for color photography according to the present invention are optically sensitized by suitable sensitizing dyes to impart sensitivities in desired spectral wave length regions to the respective emulsions. Various sensitizing dyes may be used for this purpose, and these sensitizing dyes may be employed singly or in the form of mixtures of two or more of them. Sensitizing dyes that can be used advantageously in the present invention include, in general, methine dyes such as cyanine dyes, merocyanine dyes, hemicyanine dyes, rhodacyanine dyes, oxanol dyes and hemioxanol dyes, and styryl dyes.

Dye image-forming couplers may be incorporated into the multi-layer silver halide photosensitive material for color photography according to the present invention. As useful couplers, there can be mentioned open-chain Ketomethylene type yellow couplers, pyrazolone type magenta couplers, and phenol or naphthol type cyan couplers. In combination with these couplers, azo type colored couplers for auto-masking, oxazone type compounds and diffusible dye-releasing type couplers may be employed. Open-chain Ketomethylene compounds have heretofore been used as yellow couplers, and for example, pivalyl acetoanilide type yellow couplers and benzoyl acetoanilide type yellow couplers are effective. Moreover, so called two-equivalent type couplers which are substituted at the active position by an -O-allyl or -O-acyl group, a hydantoin compound, a urazole compound, a succinimide compound, a monooxoimide compound, a pyridazone compound, fluorine, chlorine, bromine or an -O-sulfonyl group can be effectively used as yellow couplers.

As the magenta coupler that can be used in the present invention, there can be mentioned, for example, pyrazolone type compounds, pyrazolotriazole compounds, pyrazolinobenzimidazole compounds and indazolone compounds.

As the cyan coupler that can be effectively used in the present invention, there can be mentioned various phenol compounds, naphthol compounds and naphthol compounds which are substituted at the active position by an -O-aryl group.

As the colored magenta coupler, there may be used magenta coupler compounds in which the active position is substituted by an arylazo or heteroarylazo group.

As the colored cyan coupler, there can be employed masking couplers in which the active position is substituted with an arylazo group and masking couplers which react with an oxidation product of a developing agent to form a dye which is eluted into a treating bath. In addition to these couplers, there may be employed competing couplers (such as citrazinic acid), Weiss couplers and development inhibitor-releasing couplers.

In the multi-layer silver halide photosensitive material for color photography according to the present invention, various photographic additives customarily used in this field, such as film hardening agents, contrast adjusting agents, development promotors, stabilizers, ultraviolet absorbers, latent image stabilizing agents, formaline resistance-improving agents, image stabilizing agents, fluorescent whitening agents, anti-stain agents, lubricants, chelating agents, surface active agents, mordants, antistatic agents, agents for preventing color turbidity, viscosity increasing agents, gelatin plasticizers, latices and matting agents may be incorporated in silver halide emulsion layers or auxiliary layers.

As the film hardening agent, there are employed those customarily used in this field, for example, aldehyde type compounds, aziridine type compounds, isooxazole type compounds, epoxy type compounds, vinylsulfone type compounds, acryloyl type compounds, carbodiimide type compounds, maleimide type compounds, acetylene type compounds, methanesulfonic acid ester type compounds, mucohalogenoic acid type compounds, macromolecular compounds and triazine type compounds.

When such film hardening agent is used for the multi-layer silver halide photosensitive material for color photography according to the present invention, it may be incorporated in advance in a coating solution or it may be added to a coating solution continuously just before the coating operation by using an apparatus such as one disclosed in U.S. Pat. No. 3,286,992.

As the contrast adjusting agent, there may be employed metals of Group 8 of the Periodic Table, such as rhodium and ruthenium, and cadmium and thallium.

As the development promotor, there can be employed benzyl alcohol and polyoxyethylene type compounds, and intended effects can be obtained even when these compounds are incorporated in treating baths.

As the stabilizer, there can be mentioned, for example, 5,6-trimethylene-7-hydroxy-S-triazolo(1,5-a)pyrimidine, 5,6-tetramethylene-7-hydroxy-S-triazolo(1,5-a)pyrimidine, 5-methyl-7-hydroxy-S-triazolo(1,5-a)pyrimidine, 7-hydroxy-S-triazolo(1,5-a)pyrimidine, 5-methyl-6-bromo-7-hydroxy-S-triazolo(1,5-a)pyrimidine, gallic acid esters (such as isoamyl gallate, dodecyl gallate, propyl gallate and sodium gallate), mercaptans (such as 1-phenyl-5-mercaptotetrazole and 2-mercaptobenzthiazole), benzotriazoles (such as 5-bromobenztriazole), and benzimidazoles (such as 4-nitrobenzoimidazole).

Various ultraviolet absorbers can be used in the present invention. Especially good results are obtained when ultraviolet absorbers manufactured by Ciba Geigy, such as Tinuvin PS, Tinuvin 320, Tinuvin 326, Tinuvin 327 and Tinuvin 328, are used singly or in combination.

As the image-stabilizing agent, there may be employed couromane type compounds, coumarane type compounds, bisphenol type compounds and phosphorous acid ester type compounds. Among these compounds, 6,6'-butylidene-bis(2-t-butyl-4-methylphenol), 4,4'-methylene-bis(2,6-di-t-butylphenol) and 2,2'-dimethyl-4,4'-dihydroxy-5,5'-di-t-butyl-diphenyl sulfide are especially preferably employed.

As the fluorescent bleaching agent, there can be used, for example, compounds disclosed in Japanese Patent Publication No. 7127/59.

As the anti-stain agent, there may be effectively employed, for example, 2-methyl-5-hexadecylhydroquinone, 2-methyl-5-sec-octadecylhydroquinone, 2,5-di-t-octylhydroquinone and mixtures thereof.

As the lubricant, there may be employed waxes, higher fatty acid glycerides and higher alcohol esters of higher fatty acids.

Ethylenediamine tetraacetate and the like can be used as the chelating agent.

Various surface active agents, such as anionic, cationic, non-ionic and amphoteric surface active agents can be used as coating aids, emulsifiers, agents for improving the permeability in treating solutions, defoaming agents and agents for controlling various physical properties of photosensitive materials. Preferred surface active agents include anionic surface active agents such as sodium alkylsulfosuccinates (such as sodium di-2-ethylhexylsulfosuccinate and sodium amyldecylsulfosuccinate), sodium alkylbenzenesulfonates (such as sodium dodecylbenzenesulfonate) and sodium alkylnaphthalenesulfonates (such as sodium tri-iro-propyl-naphthalenesulfonate), non-ionic surface active agents such as saponin, polyethylene glycol, alkylphenoxypolyethylene glycol, alkylphenoxy glycidol, fatty acid esters of sucrose and organosiloxane-containing non-ionic surface active agents (such as Polone SR manufactured by Shinetsu Kagaku and L-76 and L-520 manufactured by Union Carbide Corporation), amphoteric surface active agents such as sodium alkylphenoxypolyethylene glycol sulfonates (such as sodium p-t-octylphenoxypolyethylene glycol sulfonate) and N-alkyl-N,N-dipolyoxyethylene-N-carboxymethyl-betaines (such as N-lauryl-N,N-dipolyoxyethylene-N-carboxymethylbetaine), and non-ionic, anionic and cationic betaine type active agents containing a fluorine-containing alkyl group (such as FC-134 and FC-172 manufactured by 3M Company). These surface active agents may be used singly or in the form of a mixture of two or more of them.

As the mordant, there may be employed N-guanylhydrazone type compounds, quaternary onium salt compounds, tertiary amine compounds and quaternary ammonium salt compounds.

As the antistatic agent, there may be effectively employed, for example, diacetyl cellulose, styrene-perfluoroalkyl sodium maleate copolymers, alkali salts of reaction products between styrene-maleic anhydride copolymers and p-aminobenzenesulfonic acid, and polyadducts formed from p-xylidine di-chloride and N,N,N',N'-tetramethyltrimethylene diamine.

As the agent for preventing color turbidity, there may be used a polymer containing a monomer of vinyl pyrrolidone, a polymer containing a monomer of vinyl oxazolidinone, a polymer containing a monomer of vinyl imidazole, and the like.

As the matting agent, there may be effectively employed poly(methyl methacrylate), polystyrene and alkali-soluble polymers (such as methyl methacrylate-methacrylic acid copolymers). Further, colloidal silicon oxide can be used.

As the latex for improving physical properties of films, there can be employed copolymers of acrylic acid esters or vinyl esters with other ethylene group-containing monomers.

As the gelatin plasticizer, there may be employed glycerine and compounds disclosed in Japanese Patent Publication No. 4939/68, etc.

As the viscosity increasing agent, there may be employed, for example, styrene-sodium maleate copolymers and alkyl vinyl ether-maleic acid copolymers.

Auxiliary layers such as filter layers, anti-halation layers and irradiation layers may be formed in the multi-layer silver halide photosensitive material for color photography according to the present invention. Dyes that can be eluted out from the photosensitive material at the development step or can be bleached are incorporated in these auxiliary layers. As typical instances of such dye, there can be mentioned cyanine dyes, merocyanine dyes, stylyl dyes, benzilidene dyes, cinnamylidene dyes, oxanole dyes, azo dyes, anthraquinone dyes and triphenylmethane dyes.

The multi-layer silver halide photosensitive material for color photography according to the present invention is formed by coating on a support silver halide emulsion layers and other structural layers into which the above-mentioned various photographic additives are optionally incorporated according to need. As the support that can be advantageously used, there can be mentioned, for example, baryta paper, polyethylene-coated paper, polypropylene artificial paper, glass sheet, and films of cellulose acetate, cellulose nitrate, polyvinyl acetal, polypropylene, polyesters such as polyethylene terephthalate, polyamides, polycarbonates and polystyrene. A suitable support is chosen appropriately depending on the intended use of the multi-layer silver halide photosensitive material for color photography.

The support may be subjected to the undercoating treatment according to need. As typical instances of the undercoating material, there csn be mentioned copolymers of vinyl chloride or vinylidene chloride, copolymers of vinyl alcohol esters, copolymers of acrylic or methacrylic acid esters, copolymers containing an unsaturated carboxylic acid, copolymers of dienes such as butadiene, copolymers of acetals, copolymers of unsaturated carboxylic acids such as maleic anhydride, especially copolymers of unsaturated carboxylic acids with a vinyl alcohol ester such as vinyl acetate or styrene and such copolymers ring-opened by water, an alcohol or amine, cellulose derivatives such as nitrocellulose and diacetylcellulose, epoxy group-containing compounds, gelatin, modified gelatin, polyolefin copolymers, and the like. These undercoating materials are used singly, or they may be used in combination according to need. Further, a mixture of gelatin with a polyol can be used. Still further, mono- and poly-hydric phenols, their halogen-substituted products, cross-linking agents (film hardening agents) and metal oxides. In practical operation, though these undercoating materials can be used singly, it is preferred to adopt a method in which a layer of the undercoating material, a layer of a mixture of the undercoating material and gelatin and a gelatin layer are formed in order by coating, or a method in which either layer of the undercoating material or a layer of a mixture of the undercoating material and gelatin is formed on the support and a gelatin layer is then formed on the above layer by coating. Of course, the number of layers can optionally be increased by the multi-layer coating technique. Any of known coating methods can be adopted according to the intended use of the photosensitive material.

Such treatments as electron shock treatments, e.g., corona discharge and glow discharge treatments, a flame treatment, a surface roughening treatment and a ultraviolet radiation treatment treatment can be applied singly or in combination to the surface of the support. Such surface treatment may be accomplished in combination with the above undercoating treatment.

The multi-layer silver halide photosensitive material for color photography according to the present invention is exposed to light and it can be subjected to the color development according to color development customarily adopted in this field. According to the reversal development, the exposed photosensitive material is first developed with a black-and-white developer, it is then exposed to white light or treated with a bath containing a fogging agent, and then it is color-developed with a color developer.

Any other known treatment can be conducted in combination with the bleaching or bleach fixing treatment. As a typical instance, there can be mentioned a treatment method as disclosed in U.S. Pat. No. 3,582,322, according to which after the color development, the bleaching fixation treatment is conducted and then, water washing and stabilization treatments are performed according to need, and a treatment method as disclosed in U.S. Technical Disclosure No. 910,002, according to which after the color development, bleaching and fixation are performed separately and then, water washing and stabilization treatments are carried out according to need.

There is known a method in which a low silver content photosensitive material is treated with an amplifier such as hydrogen peroxide or a complex salt of cobalt. In the present invention, this treatment method can be adopted. This treatment is performed at an elevated temperature for accomplishing the treatment rapidly in a short time, but it may be carried out at room temperature or at a lower temperature in an especial case.

In case such high temperature treatment is conducted, it is possible to perform a preliminary film-hardening treatment, and in some cases use of an auxiliary bath such as a neutralization bath becomes necessary and also in the present invention such auxiliary bath treatment can be conducted. As an embodiment of such treatment, there can be mentioned treatments with Flexi-Color Chemicals. Three Chemicals and ME-4, which were developed by Eastman Kodak Co. Sufficient effects can be obtained when these treatments are applied to the present invention, and also sufficient effects can be attained by modifications or improvements of these treatment methods.

Various processors can be adopted for transfer the photosensitive material in a treating machine. For example, there can be adopted a machine lift and drain processor, a continuous sinuocidal-path processor, a roller transport processor and a belt transport processor. Instead of treatment methods in which the photosensitive material is dipped in a treating bath, there may be effectively employed a special treatment method such as a treating liquid coating or spraying method for the treatment of the silver halide photosensitive material for color photography according to the present invention.

Methods for regenerating treating solutions and methods for removing chemicals causing environmental pollution or chemicals important in view of conservation of resources, such as liquid developers, heavy metals and silver have been developed in the art, and devices for practising these methods are combined into treatment apparatuses. These treatment methods and apparatuses can optionally be employed for the treatment of the photosensitive material of the present invention. Treating agents to be used are not particularly critical, but those customarily used in this field can be used in the present invention. For example, in the present invention, there can be employed such developing agents as 3-acetamido-4-amino-N,N-diethylaniline, p-amino-N-ethyl-N-($\beta$-hydroxyethyl)aniline sulfate, N,N-diethyl-p-phenylene diamine, 2-amino-5-diethylaminotoluene, N-ethyl-N-($\beta$-methanesulfonamidoethyl)-3-methyl-4-aminoaniline, 4-amino-3-methyl-N-ethyl-N-$\beta$-methoxyethylaniline, 4-amino-N-ethyl-3-methyl-N-($\beta$-sulfoethyl)aniline, 4-amino-N,N-diethylaniline hydrochloride, 4-amino-3-methyl-N,N-diethylaniline hydrochloride, 4-amino-3-methyl-N-ethyl-N-$\beta$-(methanesulfonamido)ethylaniline sulfate hydrate, 4-amino-3-methyl-N-ethyl-N-$\beta$-hydroxyethylaniline sulfate, 4-amino-3-dmethylamino-N,N-diethylaniline sulfate hydrate, 4-amino-3-methoxy-N-ethyl-N-$\beta$-hydroxyethylaniline hydrochloride, 4-amino-3-$\beta$-(methanesulfonamido)ethyl-N,N-diethylaniline dihydrochloride and 4-amino-N-ethyl-N-(2-methoxyethyl)-m-toluidine-di-p-toluene sulfonate.

As the bleaching agent (oxidant), there can be employed, for example, dichromates, potassium ferricyanate, permanganates, iron chlorides, halogens, persulfuric acids, hydrogen peroxides, metal salts of aminopolycarboxylic acids (such as ethylenediamine tetraacetic acid-iron complex salt and trinitroacetic acid-iron complex salt), iron salts of tartaric acid, and cobalt salts disclosed in West German Pat. No. 954,475 and British Pat. No. 777,635. Furthermore, there may be effectively employed quinone type bleaching agents disclosed in U.S. Pat. No. 2,507,183 and U.S. Pat. No. 2,529,981, nitroso type bleaching agents disclosed in U.S. Pat. No. 2,705,201, copper complex salt bleaching agents disclosed in British Pat. No. 774,194, Japanese Pat. Publication No. 1478/60 and British Pat. No. 1,032,024, and halogencontaining bleaching agents disclosed in U.S. Pat. No. 3,264,107 and Japanese Patent Publication No. 11068/66.

As the fixing agent, there can be employed, for example, thiosulfates, thiocyanates, thioether-polycarboxylic acids disclosed in U.S. Pat. No. 2,748,000, and bissulfonylalkane type fixing agents disclosed in Japanese Patent Application Laid-Open Specification No. 330/72.

Various agents for promoting bleaching or fixation may be used according to need. These promotors are incorporated, in many cases, into bleaching fixation baths. As typical instances of such promotor, there can be mentioned polyethylene oxide type compounds, thiourea type compounds, mercaptan type compounds, amine type compounds, onium type compounds and selenium compounds.

When an actually applicable treating solution is prepared by using the foregoing chemicals, various auxiliary agents such as pH adjusting agents, e.g., phosphoric acid, oxalic acid, citric acid, tartaric acid and boric acid, and their alkali metal salts and ammonium salts are employed. In general, antioxidants, development promotors and the like are generally incorporated into liquid developers and the like. In the present invention, any of the treatments using the foregoing various chemicals can be effectively adopted.

The present invention will now be illustrated in detail by reference to the following Examples that by no means limit the scope of the present invention.

EXAMPLE 1

Samples I and II were prepared in the following manner.

SAMPLE I 0.2 g of illustrative compound I-2 and 2.0 g of 1-hydroxy-2-[$\Lambda$-(2,4-di-t-amylphenoxy)-n-butyl]-naphthamide as a cyan coupler were dissolved in 5 ml of ethyl acetate and 2.0 ml of dibutyl phthalate at a temperature elevated to 60° C. Then, 40 ml of a 5% aqueous solution of Alkanol B (manufactured by E. I. Du Pont de Nemours & Co.) and 25 ml of a 5% aqueous solution of gelatin were added to the solution, and the mixture was emulsified and dispersed.

Then, the so prepared dispersion was added to 100 ml of a red-sensitive silver iodobromide (containing 4 mole % of slver iodide) emulsion and the mixture was dispersed. The emulsion was then coated and dried on a triacetate base.

SAMPLE II

Another sample was prepared in the same manner as described above except that the illustrative compound I-2 was not incorporated.

These samples I and II were subjected to wedge light exposure and developed at 38° C. for 3 minutes and 15 seconds by using a color developing liquid having the following composition:

Composition of Color Developing Liquid:

| | |
|---|---|
| 4-Amino-3-methyl-N-ethyl-N-($\beta$-hydroxyethyl)aniline sulfate | 4.8 g |
| Anhydrous sodium sulfite | 0.14 g |
| Hydroxyamine $\frac{1}{2}H_2SO_4$ | 1.98 g |
| Sulfuric acid | 0.74 mg |
| Anhydrous potassium carbonate | 28.85 g |
| Anhydrous potassium hydrogencarbonate | 3.46 g |
| Anhydrous potassium sulfite | 5.10 g |
| Potassium bromide | 1.16 g |
| Sodium chloride | 0.14 g |
| Trisodium nitrilotriacetate (monohydrate) | 1.20 g |
| Potassium hydroxide | 1.48 g |
| Water | balance |
| Total | 1 liter |

Then, the samples were treated in three stages for 1 minute, 2 minutes and 3 minutes, respectively, in a bleaching fixation solution having the following composition:

| Composition of Bleaching Fixation Solution: | |
|---|---|
| Hydrochloric acid (37 %) | 10 ml |
| Anhydrous sodium sulfite | 12 g |
| Ethylenediamine tetraacetate-iron-ammonium complex salt (aqueous solution of 1.1 molar concentration) | 100 ml |
| Ammonium thiosulfate (60 %) | 150 ml |
| Water | balance |
| Total | 2 liters |

Then, the samples were washed with water, subjected to the stabilization treatment and dried.

With respect to each of the foregoing developed samples, the colored dye was decolorized with gaseous hydrochloric acid, and the residual silver density in the decolorized sample (the silver density after the bleaching treatment) was measured by using a denstometer (Model KS-7R manufactured by Konishiroku Shashin Kogyo Kabushiki Kaisha).

Separately, each sample was color-developed under the same conditions as described above, and the colored dye was immediately decolorized and the silver density (the unbleached silver density) was measured. The degree of bleaching was determined based on the results of measurement of the silver density before and after bleaching to obtain results shown in Table 1.

In Table 1, the value (%) for the degree of bleaching is one calculated according to the following calculation formula:

$$\text{Degree (\%) of Bleaching} = \frac{(D - D')}{D} \times 100$$

wherein D stands for the unbleached silver density and D' stands for the silver density after the bleaching treatment.

Table 1

| | Degree of Bleaching | | |
|---|---|---|---|
| | Bleaching Time | | |
| Sample | 1 minute | 2 minutes | 3 minutes |
| Sample I | 69 % | 100 % | 100 % |
| Sample II (comparison) | 26 % | 55 % | 98 % |

From the results shown in Table 1, it will readily be understood that a high bleaching promoting effect can be attained by the use of the compound of the present invention. This fact means that the use of the compound of the present invention makes it possible to use a bleaching fixation solution of a much reduced concentration, and that the use of the compound of the present invention is advantageous in view of prevention of environmental pollution.

EXAMPLE 2

The same sample as used in Example 1 were light-exposed and color-developed in the same manner as described in Example 1, and they were treated for 1 or 3 minutes with a bleaching solution having the following composition: Composition of Bleaching Solution:

| Ethylenediamine tetraacetate-iron-ammonium complex | 100.0 g |
|---|---|
| Diammonium ethylenediamine tetraacetate | 10.0 g |
| Ammonium bromide | 150.0 g |
| Glacial acetic acid | 10.0 ml |
| Water | balance |
| Total | 1 liter |

The pH of the bleaching solution was adjusted to 6.0 by addition of aqueous ammonia.

Then, each sample was washed with water for 3 minutes and 15 seconds and subjected to the fixation treatment according to a customary method. In the same manner as described in Example 1, the sample was decolorized and the residual silver density and unbleached silver density were measured to determine the degree of bleaching. It was found that in the case of sample 1 containing the compound of the present invention, decolorization was completely accomplished by conducting the treatment for 1 minute, whereas in the case of comparative sample II, decolorization was substantially accomplished when the treatment was carried out for 3 minutes.

In view of the foregoin, it will readily be understood that the compound of the present invention exhibits an excellent effect also at the bleaching treatment.

EXAMPLE 3

2.0 or 10.0 g of illustrative compound I-6, I-7, I-12, I-14 or II-2 and 2.0 g of 1-hydroxy-2- [δ-(2,4-di-t-amyl-phenoxy)butyl] -naphthamide as a cyan coupler was dissolved in 40 ml of ethyl acetate and 20 ml of tricresyl phosphate, and an emulsified dispersion was prepared from the solution in the same manner as described in Example 1.

The dispersion was added to and dispersed in 1 Kg of a red-sensitive silver iodobrimide (containing 6.0 mole % of silver iodide) emulsion, and then, the emulsion was coated and dried on a cellulose triacetate base.

A comparative sample was prepared in the same manner as described above except that no illustrative compound was incorporated.

The so prepared samples were subjected to the wedge light exposure and then to the following treatment steps under conditions described below.
Treatment Steps:
  Preliminary film hardening: 2 minutes
  Neutralization: 1 minute
  First development: 2 minutes
  First stopping: 1 minute
  Water washing: 1 minute
  Color development: 2 minutes
  Second stopping: 1 minute
  Water washing: 1 minute
  Bleaching fixation: 4 minutes
  Water washing: 2 minutes
  Drying: 40° C.

Compositions of treating solutions used were as follows:
Composition of First Development Solution:

| Anhydrous sodium bisulfite | 8.0 g |
|---|---|
| Phenidone | 0.35 g |
| Anhydrous sodium sulfite | 37.0 g |
| Hydroquinone | 5.5 g |
| Anhydrous sodium carbonate | 28.2 g |
| Sodium thiocyanate | 1.38 g |
| Anhydrous sodium bromide | 1.30 g |
| Water | balance |
| Total | 1 liter |

Composition of Liquid Developer for Color Development:

| | |
|---|---|
| Benzyl alcohol | 4.5 ml |
| Anhydrous sodium sulfite | 7.5 g |
| Trisodium phosphate dodecahydrate | 36.0 g |
| Anhydrous sodium bromide | 0.9 g |
| Sodium iodide 0.09 g | |
| Sodium hydroxide | 3.25 g |
| Cirazinic acid | 1.50 g |
| N-ethyl-N-β-methanesulfonamideo-ethyl-3-methyl-4-aminoaniline sulfate | 11.0 g |
| Ethylene diamine | 3.0 g |
| Tertiary butylamine borane | 0.07 g |
| Water | balance |
| Total | 1 liter |

Composition of Bleaching Fixation Solution:

| | |
|---|---|
| Ethylene diamine tetraacetate-iron-ammonium complex | 45.0 g |
| Ammonium thiocyanate | 10.0 g |
| Anhydrous sodium sulfite | 10.0 g |
| Ammonium thiosulfate | 60.0 g |
| Diammonium ethylene diamine tetraacetate | 5.0 g |
| Water | balance |
| Total | 2 liter |

With respect to each of the so treated samples, the colored dye was decolorized and the residual silver density was immediately measured, and in the same manner as described in Example 1 the unbleached silver density was measured. Based on the measured values, the degree of bleaching was determined to obtain results shown in Table 2.

Table 2

| Compound Added | Amount (g) | Bleaching Time | | | |
|---|---|---|---|---|---|
| | | 0.5 minute | 1 minute | 2 minutes | 3 minutes |
| Illustrative Compound I-6 | 2 | 40 % | 72 % | 100 % | 100 % |
| | 10 | 53 % | 89 % | 100 % | 100 % |
| Illustrative Compound 1-7 | 2 | 33 % | 69 % | 98 % | 100 % |
| | 10 | 47 % | 82 % | 100 % | 100 % |
| Illustrative Compound I-12 | 2 | 31 % | 63 % | 100 % | 100 % |
| | 10 | 46 % | 80 % | 100 % | 100 % |
| Illustrative Compound I-14 | 2 | 36 % | 60 % | 100 % | 100 % |
| | 10 | 50 % | 73 % | 100 % | 100 % |
| Illustrative Compound II-2 | 2 | 28 % | 55 % | 97 % | 100 % |
| | 10 | 43 % | 78 % | 100 % | 100 % |
| Control | 0 | 15 % | 26 % | 55 % | 99 % |

From the results shown in Table 2, it is evident that each of the compounds of the present invention has a very high bleaching-promoting effect and that they are very valuable and useful for formation of photosensitive materials for reversal color photography.

EXAMPLE 4

0.3 g of illustrative compounds II-4 and 2.0 g of α-pivalyl-α-(3-benzyl-2,4-dioxo-imidazolidin-3-yl)-5-[(δ-2,4-di-t-amylphenoxy)butylamido]-2-chloracetanilide as a yellow coupler were dissolved in 3.0 ml of ethyl acetate and 1.0 ml of dibutyl phthalate, and the mixtue was emulsified and dipersed in the same manner as described in Example 1. Then, the resulting dispersion was added to 100 ml of a blue-sensitive silver chlorobromide (containing 20 mole % of silver bromide) emulsion, and the resulting coating composition was coated and dried on a polyethylene-laminated paper support.

A comparative sample was prepared in the same manner as described above except that the illustrative compound II-4 was not incorporated.

These samples were subjected to wedge light exposure and then subjected to color development at 31° C. for 3 minutes and 30 seconds according to a customary method. Then, the samples were treated at 31° C. for 1 minute with a bleaching fixation solution having the following composition:

| | |
|---|---|
| Sodium iron (II) ethylene diamine tetraacetate | 180 g |
| Ammonium thiocyanate | 200 g |
| Ammonia and sulfuric acid | amounts necessary for adjusting the pH to 5.0 |
| Water | balance |
| Total | 1 liter |

Then, the samples were washed with water for 2 minutes, dipped in an ordinary stabilizing solution for 1 minute and dried.

The silver density of the so developed samples was measured through a red filter by means of a densitometer.

As a result it was found that the sample containing the compound of the present invention was sufficiently bleached only by conducting the treatment for 1 minute, whereas the presence of residual silver was observed in the comparative sample free of the compound of the present invention even after 1 minute's treatment and the bleaching effect was insufficient.

In view of the foregoing, it is apparent that the compound of the present invention is effective even when it is applied to a photographic emulsion containing silver chloride.

What is claimed is:

1. A silver halide photosensitive material for color photography comprising a bleach-promoting substance releasing compound upon reacting with an oxidation product of a color developing agent, said bleach-promoting substance-releasing compound being represented by the following general formulas:

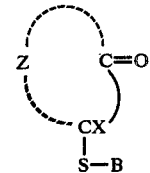
I wherein Z is a group of non-metallic atoms necessary for forming a 5-, 6- or 7-membered saturated or unsaturated carbon ring or nitrogen, oxygen, or sulfur containing heterocyclic ring wherein said carbon ring and said carbon ring and said heterocyclic ring may be substituted with at least one member selected from the group consisting of alkyl, aryl, alkoxy, aryloxy, halogen and a group-SB, in which ring the two substituents can form a condensed ring, X is hydrogen or halogen, and B is a group capable of forming, together with the sulphur atom, a heterocyclic mercapto compound selected from the group consisting of 1H-2-mercaptotetrazole, 3-mercapto-1,2,4-triazole, 3-mercapto-4-phenyl-5-amino-1,2,4-triazole, mercapto imidazoline, mercapto pyrimidine, mercapto purine, mercapto quinolidine and 2-mercapto-5-amino-1,4,5-thiadiazole, or:

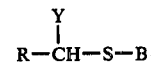
II wherein Y is a halogen or a group —OR₁ or —COOR₂ in which R₁ is alkyl, aryl, acyl or heterocyclic group, R₂ is alkyl, R is a group $$-\underset{\underset{O}{\|}}{C}-R_3, \quad -\underset{\underset{O}{\|}}{C}-NH_2, \quad -\underset{\underset{O}{\|}}{C}-NHR_3, \quad -\underset{\underset{O}{\|}}{C}-N\diagup_{R_3}^{R_3}$$

or —COOR₄ in which R₃ is alkyl, aryl, or a heterocyclic group with the proviso that in the case of a group having two R₃s, two R₃s can jointly form a nitrogen-containing ring and R₄ is alkyl, and B is as defined in the general formula I.

2. The silver halide photosensitive material according to claim 1 wherein Z is a member selected from the group consisting of cyclopentanone, cyclohexanone indanone, tetralone, piperidone, 4- to 7-membered lactones, lactam, and hydantoin.

3. The silver halide photosensitive material according to claim 1 wherein the heterocyclic mercapto compound is 1H-2-mercaptotriazole.

4. The silver halide photosensitive material according to claim 1 wherein the heterocyclic mercapto compound is mercaptotriazole.

5. The silver halide photosensitive material according to claim 1 wherein the heterocyclic mercapto compound is mercapto imidazoline.

6. The silver halide photosensitive material according to claim 1 wherein the heterocyclic mercapato compound is mercapto pyrimidine.

7. The silver halide photosensitive material according to claim 1 wherein the heterocyclic mercapto compound is mercapto purine.

8. The silver halide photosensitive material according to claim 1 wherein the heterocyclic mercapto compound is mercapto quinolidine.

9. The silver halide photosensitive material according to claim 1 wherein the heterocyclic mercapto compound is mercapto thiadiazole.

10. The silver halide photosensitive material according to claim 1 wherein the heterocyclic mercapto compound is 3-mercapto-1,2,4-triazole.

11. The silver halide photosensitive material according to claim 1 wherein the heterocyclic mercapto compound is 3-mercapto-4-phenyl-5-amino-1,2,4-triazole.

12. The silver halide photosensitive material according to claim 1 wherein the heterocyclic mercapto compound is 2-mercapto imidazoline.

13. The silver halide photosensitive material according to claim 1 wherein the heterocyclic mercapto compound is 2-mercapto-4-pyrimidine.

14. The silver halide photosensitive material according to claim 1 wherein the heterocyclic mercapto compound is 2-amino-4-mercaptopurine.

15. The silver halide photosensitive material according to claim 1 wherein the heterocyclic mercapto compound is 4-mercapto-4H-quinolidine.

16. The silver halide photosensitive material according to claim 1 wherein the heterocyclic mercapto compound is 2-mercapto-5-amino-1,4,5-thiadiazole.

17. The silver halide photosensitive material of claim 1 wherein the bleach-promoting substance is selected from the group consisting of:

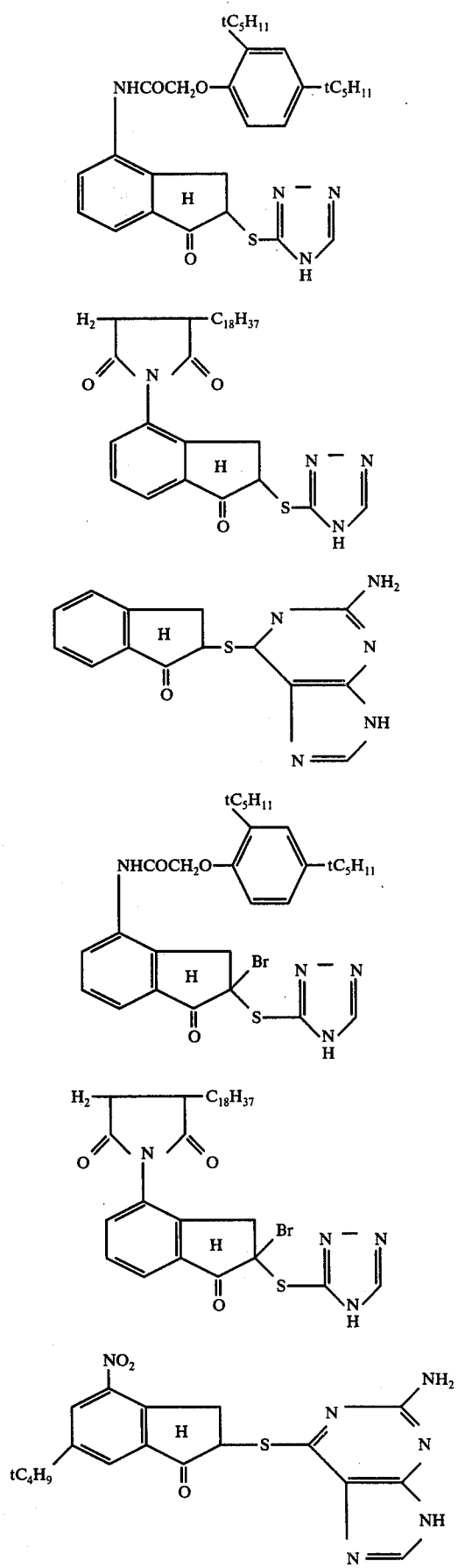

-continued
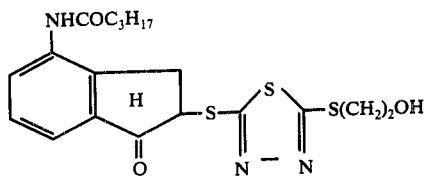
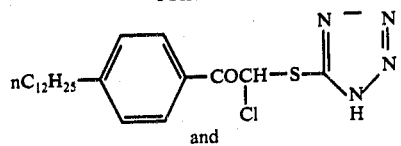
and
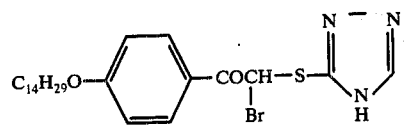
* * * * *